US006584352B2

(12) United States Patent
Combs et al.

(10) Patent No.: US 6,584,352 B2
(45) Date of Patent: Jun. 24, 2003

(54) LEADLESS FULLY AUTOMATIC PACEMAKER FOLLOW-UP

(75) Inventors: William J. Combs, Minnetonka, MN (US); Gary Berg, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 294 days.

(21) Appl. No.: 09/749,169

(22) Filed: Dec. 27, 2000

(65) Prior Publication Data

US 2002/0123770 A1 Sep. 5, 2002

(51) Int. Cl.[7] ............................................. A61N 1/362
(52) U.S. Cl. ............................. 607/9; 607/32; 607/60
(58) Field of Search .................................. 600/300, 301; 607/4, 5, 9, 30, 32, 60, 59; 128/903, 904

(56) References Cited

U.S. PATENT DOCUMENTS

| | | | |
|---|---|---|---|
| 3,757,792 A | 9/1973 | Mulier et al. ............... 607/11 |
| 3,920,024 A | 11/1975 | Bowers ..................... 607/28 |
| 3,949,758 A | 4/1976 | Jirak ........................ 607/28 |
| 3,977,411 A | 8/1976 | Hughes, Jr. et al. ........... 607/9 |
| 4,023,565 A | 5/1977 | Ohlsson .................... 600/522 |
| 4,121,576 A | 10/1978 | Greensite .................. 600/512 |
| 4,136,690 A | 1/1979 | Anderson et al. ........... 600/512 |
| 4,170,227 A | 10/1979 | Feldman et al. ............ 600/517 |
| 4,216,780 A | 8/1980 | Rubel et al. ............... 600/512 |
| 4,250,884 A | 2/1981 | Hartlaub et al. ............ 607/30 |
| 4,263,919 A | 4/1981 | Levin ...................... 600/521 |
| 4,310,000 A | 1/1982 | Lindemans ................. 607/38 |
| 4,365,639 A | 12/1982 | Goldreyer ................. 607/122 |
| 4,476,868 A | 10/1984 | Thompson ................. 607/14 |
| 4,593,702 A | 6/1986 | Kepski et al. .............. 600/509 |
| 4,630,611 A | 12/1986 | King ....................... 600/377 |
| 4,674,508 A | 6/1987 | DeCote .................... 607/28 |
| 4,712,554 A | 12/1987 | Garson, Jr. ................. 607/9 |
| 4,729,376 A | 3/1988 | DeCote, Jr. ................ 607/28 |
| 4,754,753 A | 7/1988 | King ....................... 600/512 |
| 4,759,366 A | 7/1988 | Callaghan .................. 607/26 |
| 4,858,610 A | 8/1989 | Callaghan et al. ........... 607/13 |
| 4,967,746 A | 11/1990 | Vandegriff .................. 607/9 |
| 5,127,401 A | 7/1992 | Grevious et al. ............. 607/27 |
| 5,331,966 A | 7/1994 | Bennett et al. .............. 600/508 |
| 5,383,915 A * | 1/1995 | Adams ..................... 607/60 |
| 5,720,770 A | 2/1998 | Nappholz et al. ............ 607/30 |
| 5,752,976 A * | 5/1998 | Duffin et al. ............... 607/32 |
| 5,759,199 A | 6/1998 | Snell et al. ................. 607/60 |
| 6,083,248 A * | 7/2000 | Thompson ................. 607/30 |
| 6,292,698 B1 * | 9/2001 | Duffin et al. ............... 607/32 |
| 6,442,432 B2 * | 8/2002 | Lee ........................ 607/59 |
| 6,480,745 B2 * | 11/2002 | Nelson et al. .............. 607/60 |

FOREIGN PATENT DOCUMENTS

| EP | 0086429 | 8/1989 |
|---|---|---|
| EP | 0 362 611 | 11/1990 |

OTHER PUBLICATIONS

Brabec, S. et al., "Subcutaneous Spiral Electrode for Sensing Electrical Signals of the Heart", U.S. patent application Ser. No. 09/703,152 (Filed Oct. 31, 2000).

(List continued on next page.)

Primary Examiner—Willis R. Wolfe
(74) Attorney, Agent, or Firm—Girma Wolde-Michael

(57) ABSTRACT

A leadless fully automatic follow-up (LFAPF) device that is triggered into operation either locally or remotely is implemented extra-corporeally to access cardiac data such as ECGs stored in one or more implantable medical device (IMDs) implanted in one or more patients. A telemetry unit is used in the LFAPF to transmit and test stored data in the IMDs. The telemetry unit implements a series of adjustable commands depending on the desired level of detail of the follow-up. An alternate embodiment representing intra-corporeal use of an additional device includes cardiac data monitoring and cardioversion pulse synchronization in cooperation with another IMD such as a pacer.

22 Claims, 6 Drawing Sheets

OTHER PUBLICATIONS

Ceballos, T. et al., "Surround Shroud Connector and Electrode Housings for a Subcutaneous Electrode Array and Leadless ECGs", U.S. patent application Ser. No. 09/697,438 (Filed Oct. 26, 2000).

Goldreyer, B. et al., "Orthogonal Electrogram Sensing", *PACE*, vol. 6, pp. 464–469 (Mar.–Apr. 1983, Part II).

Goldreyer, B., et al., "Orthogonal Ventricular Electrogram Sensing", *PACE*, vol. 6, pp. 761–768 (Jul.–Aug. 1983).

Guck, B. et al., "Multilayer Ceramic Electrodes for Sensing Cardiac Depolarization Signals", U.S. patent application Ser. No. 09/696,365 (Filed Oct. 25, 2000).

Guck, B. et al., "Thin Film Electrodes For Sensing Cardiac Depolarization Signals", U.S. patent application Ser. No. 09/736,046 (Filed Dec. 13, 2000).

Lee, B. et al., "System and Method for Deriving a Virtual ECG or EGM Signal", U.S. patent application Ser. No. 09/721,275 (Filed Nov. 22, 2000).

Reddy, B.R.S. et al., "Rhythm Analysis Using Vectorcardiograms", *IEEE Transactions on Biomedical Engineering*, vol. BME–32, No. 2, pp. 97–104 (Feb. 1985).

* cited by examiner

LEADLESS FULLY AUTOMATIC PACEMAKER FOLLOW-UP

FIELD OF THE INVENTION

This invention relates to sensing of cardiac activity via electrocardiographic (ECG) data. In particular, this invention relates to a new and improved method of gathering ECG data and to the transmission of the collected data to a remote location for analysis. Alternatively, such ECG data may also be transmitted to a co-implanted device to provide data for the delivery of various therapies including pacing, cardioversion and defibrillation therapies, drug delivery, to effect capture detection and automatic stimulation threshold adaptation, to record PMT (pacemaker mediated tachycardia) episodes, to measure refractory periods, to set timing windows for anti-tachycardia pacing therapies, and to adjust the pacing rate to physiologic demand.

BACKGROUND OF THE INVENTION

The electrocardiogram (ECG) is commonly used in medicine to determine the status of the electrical conduction system of the human heart. As currently practiced, the ECG recording device is commonly attached to the patient via ECG leads connected to pads arrayed on the patient's body so as to achieve a recording that displays the cardiac waveforms in any one of 12 possible vectors.

The detection and discrimination between various arrhythmic episodes in order to trigger the delivery of an appropriate therapy is of considerable interest. Prescription for implantation and programming of the implanted device are based on the analysis of the PQRST electrocardiogram (ECG) that currently requires externally attached electrodes and the electrogram (EGM) that requires implanted pacing leads. The EGM waveforms are usually separated for such analysis into the P-wave and R-wave in systems that are designed to detect the depolarization of the atrium and ventricle respectively. Such systems employ detection of the occurrence of the P-wave and R-wave, analysis of the rate, regularity, and onset of variations in the rate of recurrence of the P-wave and R-wave, the morphology of the P-wave and R-wave and the direction of propagation of the depolarization represented by the P-wave and R-wave in the heart. The detection, analysis and storage of such EGM data within implanted medical devices are well known in the art. Acquisition and use of ECG tracing(s), on the other hand, has generally been limited to the use of an external ECG recording machine attached to the patient via surface electrodes of one sort or another.

Recently, however, an alternative method of collecting ECG tracings from a set of subcutaneous electrodes, or a subcutaneous electrode array (SEA), has been described in the following patents or patent applications. U.S. Pat. No. 5,331,966 to Bennett, incorporated herein by reference, discloses a method and apparatus for providing an enhanced capability of detecting and gathering electrical cardiac signals via an array of relatively closely spaced subcutaneous electrodes (located on the body of an implanted device).

More recently, a patent application entitled "*Surround Shroud Connector and Electrode Housings for a Subcutaneous Electrode Array and Leadless ECGs*", by Ceballos, et al., filed on Oct. 26, 2000, Ser. No. 09/697,438, incorporated herein by reference in its totality, discloses an alternate method and apparatus for detecting electrical cardiac signals via an array of subcutaneous electrodes located on a shroud circumferentially placed on the perimeter of an implanted pacemaker. Similarly, a patent application entitled "*Subcutaneous Electrode for Sensing Electrical Signals of the Heart*", by Brabec et al, filed Oct. 31, 2000, Ser. No. 09/703,152, incorporated herein by reference in its totality, discloses the use of a spiral electrode using in conjunction with the shroud described in the Ceballos et al disclosure. In addition, two applications, entitled "*Multilayer Ceramic Electrodes for Sensing Cardiac Depolarization Signals*", by Guck et al, filed Oct. 25, 2000, Ser. No. 09/696,365 and P-8787 "*Thin Film electrodes for Sensing Cardiac Depolarization Signals*" by Guck and Donders, filed Dec. 13, 2000, Ser. No. as yet unknown, both incorporated herein by reference in their totality, disclosed the use of sensing electrodes placed into recesses incorporated along and into the peripheral edge of the implantable pacemaker. Finally, the submission entitled, "*Subcutaneous Electrode Array Virtual ECG Lead*" by Panken and Reinke, filed Nov. 22, 2000, Ser. No. 09/721,275, also incorporated by reference to its entirety, describes the algorithm used by the implanted device that compiles the ECG from any two subcutaneous electrodes found in the SEA.

As the functional sophistication and complexity of implantable medical device systems increased over the years, it became increasingly more important for such systems to include a system for facilitating communication between one implanted device and another implanted device and/or an external device, for example, a programming console, monitoring system, or the like. For diagnostic purposes, it is desirable that the implanted device be able to communicate information regarding the device's operational status and the patient's condition to the physician or clinician. State of the art implantable devices are available which can even transmit a digitized electrical signal to display electrical cardiac activity (e.g., an ECG, EGM, or the like), programmed pacing parameters, therapy status, etc. for storage and/or analysis by an external device.

To diagnose and measure cardiac events, the cardiologist has several tools from which to choose. Such tools include twelve-lead electrocardiograms, exercise stress electrocardiograms, Holter monitoring, radioisotope imaging, coronary angiography, myocardial biopsy, and blood serum enzyme tests. In addition, a record of the programmed parameters, the status of atrial and ventricular auto-capture, the atrial and ventricular sensing threshold, and other such pacing system parameters are required for an adequate diagnosis. Such ECG tracings and printed reports are placed into the patient's records and used for comparison to more recent tracings and reports. It must be noted, however, that whenever an ECG recording is required (whether through a direct connection to an ECG recording device or to a pacemaker programmer), external electrodes and leads must be used. Moreover, the acquisition of programmed data and pacing therapy status requires the use of a programming system that is in immediate proximity to the patient.

Unfortunately, surface ECG electrodes have some serious drawbacks. For example, electrocardiogram analysis performed using existing external or body surface ECG systems is likely to be limited by mechanical problems and poor signal quality. Electrodes attached externally to the body are a major source of signal quality problems and analysis errors because of susceptibility to interference such as muscle noise, power line interference, high frequency communication equipment interference, and baseline shift from respiration or motion. Signal degradation also occurs due to contact problems, ECG waveform artifacts, and patient discomfort. Externally attached electrodes are subject to motion artifacts from positional changes and the relative displacement between the skin and the electrodes. Furthermore, external electrodes require special skin preparation to ensure adequate electrical contact. Such preparation, along with positioning the electrode and attachment of the ECG lead to the electrode needlessly prolongs the pacemaker follow-up session. One possible approach is to equip the implanted pacemaker with the ability to detect cardiac signals, transform them into a tracing, and transmit them to a remote receiving device such as a programmer, transtelephonic pacemaker monitoring system, or a central database system. Once captured, these ECG tracing could be available for use by medical personnel for analysis and diagnosis.

Similarly, it is often difficult if not impossible to have a programming unit nearby to gain a visual or printed report or all the various programmed parameters and the status of the associated pacing therapies. For example, when a physician visits a hospitalized patient, it is now mandatory that he or she carry a programmer to the patient's bedside to acquire a full status of the pacemaker's operation. If, for one reason or another, the physician has no programmer immediately available, he or she must take the time to retrace steps and find one to bring back to the patient's bedside. It would certainly be advantageous if that patient's ECG and pacemaker status could be acquired remotely prior to the physician's approach to the bedside. In addition, when a pacemaker patient visits his or her physician, there is often a period of time that the patient sits in the waiting room. This time could be advantageously to capture the patient's ECG data as well as the pacemaker's programmed status via a transmission to a programmer located in the pacemaker technician's office. Then, these reports could be printed and made available to the physician for study prior to bringing the patient into the pacemaker clinic. The patient, especially the female patient, would feel more comfortable, not having to disrobe to complete the pacemaker follow-up session.

As pacing and other medical technology have advanced, it is often necessary to co-implant other implantable devices such as a cardioverter-defibrillator, drug delivery system, a pressure sensor, and so on. Each of these devices may require ECG data upon which to make therapy and diagnostic decisions. Thus the ECG data already available in the implanted pacemaker may be transmitted intracorporeally to provide control signals for the delivery of various therapies including pacing, cardioversion and defibrillation therapies as well as the delivery of antiarrhythmic drugs, and, in the pacing context, to effect capture detection and automatic stimulation threshold adaptation, recording of PMT episodes, measurement of refractory periods in order to set timing windows for antitachycardia pacing therapies, and as a control signal for use in adjusting pacing rate to physiologic demand. All these devices would benefit from enhanced capabilities of discriminating cardiac arrhythmias and storing the associated data.

As used herein, Capture is defined as an evoked cardiac response to a pacemaker output or stimulation pulse. In a dual chamber pacemaker, for example, a stimulation pulse can be applied to either the atrium or the ventricle during the appropriate portion of a cardiac cycle. The minimum output pulse energy required to capture and thus evoke a cardiac depolarization is referred to as the stimulation threshold. This threshold generally varies in accordance with the well known strength-duration curves, wherein the amplitude of a stimulation threshold current pulse and its duration are inversely proportional.

A number of factors can influence changes in the stimulation threshold following implantation of the pacemaker and pacing lead. These include: (1) changes in position of the pacing electrode relative to the cardiac tissue; (2) long-term biologic changes in cardiac tissue closely adjacent the electrode, such as fibrotic tissue growth; (3) changes in the patient's sensitivity to stimulation as a function of periodically fluctuating conditions, even on a daily basis, due to various causes such as diet, exercise, administered drugs, electrolyte changes, etc.; and (4) gradual changes in pacemaker/lead performance due to various causes such as battery depletion, component aging, etc.

Capture Threshold Detection and Adjustable Output Pulse Energy require that battery power be conserved to extend the pacemaker's useful life. It is therefore desirable to achieve capture at the lowest possible settings (amplitude and pulse width) for the output pulse. With the advancement of programmable pacemakers, it became common to initially program an output pulse energy setting which includes a safety margin somewhat above that required to produce capture. These programmable pacemakers include programmable options that permit the physician to select output pulse settings known to be sufficient to capture the heart but which are below the maximum obtainable output voltage of the pacemaker. The attending physician usually determines such output pulse adjustments during an office visit with the use of an external programmer and an electrocardiogram (ECG) monitor. At this time, the physician assesses capture by means of an ECG, while at the same time the pacemaker is providing a sequence of temporarily programmed-in stimulation pulses with decreasing pulse voltages in a system of the type described in U.S. Pat. No. 4,250,884 to Hartlaub, et al. For example, capture detection of the ventricle is confirmed by the presence of the evoked QRS complex or R-wave, and capture detection of the atrium is confirmed by the presence of the evoked P-wave. Loss of capture can be directly observed and correlated to the pulse energy at which capture is lost.

Since the late 1960's, self-adaptive pacemakers have been developed that have the capability of automatically adjusting the voltage of the pacing pulse as appropriate to accommodate changes in stimulation threshold.

U.S. Pat. No. 3,757,792 to Mulier et al, for example, relates to an early pacemaker that provides for a decreased battery drain by sensing each driven heart beat (i.e., R-wave) and providing for a decrease in energy for each succeeding output pulse until such time as loss of capture is detected. Following a detected loss of capture, the next succeeding output pulse is increased in voltage by an amount to be safely over the threshold hysteresis level. U.S. Pat. No. 3,949,758 to Jirak (incorporated herein by reference) relates to a similar threshold-seeking pacemaker with automatically adjusted voltage levels for output pulses in response to detected loss of capture (i.e., absence of R-wave), and describes separate sensing and pacing electrodes, which are each utilized in unipolar fashion with a third common electrode having a comparatively larger dimension, to reduce residual polarization problems.

U.S. Pat. No. 3,977,411 to Hughes, Jr. et al shows a pacemaker having separate sensing and pacing electrodes that are each utilized in unipolar fashion. The sensing electrode comprises a ring electrode having a relatively large surface area (i.e., between 75 to 200 mm.sup.2) for improved sensing of cardiac activity (R-waves), and is spaced along the pacing lead approximately 5 to 50 mm from the distally-located tip electrode used for pacing.

U.S. Pat. No. 3,920,024 to Bowers shows a pacemaker with a threshold tracking capability that dynamically measures the stimulation threshold by monitoring the presence or absence of an evoked response (R-wave). If no R-wave is sensed within a post-stimulus interval (e.g., 20 to 30 ms post-stimulus), the pacemaker delivers a closely spaced backup pulse (e.g., 40 to 50 ms post-stimulus) at increased amplitude and pulse width to ensure an evoked response.

U.S. Pat. Nos. 4,759,366 and 4,858,610 to Callaghan, et al, incorporated herein by reference, relate to evoked response detector circuits which also employ fast recharge in at least one separate sensing electrode in either unipolar or bipolar electrode configurations in either or both the atrium and ventricle. The cardiac pacing systems function as unipolar and bipolar systems at different steps in the operating cycle. In the '610 patent, a separate electrode on the connector block of the pacemaker can is suggested for use as the reference electrode anode rather than the metal case itself if the case is employed as the reference electrode for the delivery of the stimulation pulse. In the '366 patent, the detected evoked response is used in an algorithm for adjusting the pacing rate.

U.S. Pat. No. 4,310,000 to Lindemans and U.S. Pat. Nos. 4,729,376 and 4,674,508 to DeCote, incorporated herein by reference, also disclose the use of a separate passive sensing reference electrode mounted on the pacemaker connector block or otherwise insulated from the pacemaker case in order to provide a sensing reference electrode which is not part of the stimulation reference electrode and thus does not have residual after-potentials at its surface following delivery of a stimulation pulse. The DeCote '376 and '508 patents also set forth stimulation threshold testing algorithms for adjusting the pacing pulse energy.

Thus, considerable effort has been expended in providing electrode systems, fast recharge circuitry and separate sense amplifier systems for avoiding after-potentials and providing capture detection and stimulation threshold tracking.

Distinguishing malignant tachyarrhythmias from sinus tachycardias and detecting pacemaker mediated tachycardias is similarly limited by the available electrode configurations employed in single and dual chamber pacing systems, implantable drug dispensers and pacemaker-cardioverter-defibrillator systems as described above. In the context of discriminating spontaneously occurring tachyarrhythmias from sinus tachycardia, attempts have been made to employ both atrial and ventricular electrode systems in order to determine whether the tachycardia is sinus in origin or reflects a retrogradely conducted abnormal ventricular rhythm. For example, previous art has placed multiple electrodes on atrial and ventricular leads and to sense the direction of travel of a depolarization wave front as shown for example in U.S. Pat. No. 4,712,554 to Garson, Jr.

In addition, other art has shown that pacemakers that operated in the DDD or related modes can, under certain circumstances, sustain a dangerous tachycardia with ventricular pacing at the upper rate limit, a pacemaker mediated tachycardia (PMT). A PMT may be initiated when AV synchrony is lost, leaving the AV node conductive tissue able to conduct retrograde electrical signals from the ventricle to the atrium which in turn cause an atrial depolarization. The sensing of the resulting atrial depolarization by the atrial sense amplifier in turn causes the ventricular pulse generator to emit a ventricular pacing pulse after the AV time period times out. The cycle may repeat itself if the ventricular pace event is conducted to the atrium where it again causes an atrial depolarization which is picked up by the atrial sense amplifier. This repetitive high rate stimulation may be sustained indefinitely by the pacemaker causing discomfort to the patient or possibly inducing more threatening arrhythmias.

Various techniques have been implemented to minimize the impact of PMTs, but these techniques usually sacrifice flexibility of the DDD system. U.S. Pat. No. 4,967,746 to Vandegriff sets forth a number of techniques which have been employed to alleviate PMTs.

ECG/EGM Vector Analysis——U.S. Pat. No. 4,310,000 issued to Lindemans suggests various modifications to the passive sensing reference electrode depicted in its drawings, including the incorporation of more than one passive sensing reference electrode provided on or adjacent to the metallic can, positioned as deemed necessary for best sensing, and connected to one or more sense amplifiers. No specific use of the additional passive sensing reference electrodes is suggested, although the single passive sensing reference electrode is suggested for use with a sense amplifier to detect both capture and spontaneous atrial or ventricular electrical events in a dual chamber pacing system.

It is known in the art to monitor electrical activity of the human heart for diagnostic and related medical purposes. U.S. Pat. No. 4,023,565 issued to Ohlsson describes circuitry for recording EKG signals from multiple lead inputs. Similarly, U.S. Pat. No. 4,263,919 issued to Levin, U.S. Pat. No. 4,170,227 issued to Feldman, et al, and U.S. Pat. No. 4,593,702 issued to Kepski, et al, describe multiple electrode systems which combine surface EKG signals for artifact rejection.

The primary use for multiple electrode systems in the prior art appears to be vector cardiography from EKG signals taken from multiple chest and limb electrodes. This is a technique whereby the direction of depolarization of the heart is monitored, as well as the amplitude. U.S. Pat. No. 4,121,576 issued to Greensite discusses such a system.

In addition, U.S. Pat. No. 4,136,690 issued to Anderson, et al, shows a vector cardiographic system used for arrhythmia analysis. Similar techniques are described in "Rhythm Analysis Using Vector Cardiograms," Transactions on Biomedical Engineering, Vol. BME-32, No. 2, February 1985, by Reddy, et al, European Pat. No. 0 086 429 issued to Sanz and U.S. Pat. No. 4,216,780 issued to Rubel, et al.

Various systems have additionally been proposed for measuring the orthogonal ventricular or atrial electrogram from multi-electrode lead systems placed endocardially within the patient's atrium and/or ventricle. Such orthogonal endocardial EGM systems are depicted in U.S. Pat. No. 4,365,639, issued to Goldreyer, and U.S. Pat. Nos. 4,630,611 and 4,754,753 issued to King. In addition, orthogonal ventricular electrogram sensing employing endocardial, multi-electrode lead systems and associated circuitry are disclosed in two articles by Goldreyer, et al, entitled "Orthogonal Electrogram Sensing," PACE, Vol. 6, pp. 464–469, March–April 1983, Part II, and "Orthogonal Ventricular Electrogram Sensing," PACE, Vol. 6, pp. 761–768, July–August 1983. In the Goldreyer patent and in these papers, it is suggested that the orthogonal electrodes be employed to detect paced events and provide capture verification as well as to facilitate the discrimination of P-waves from QRS complexes. Other articles by Goldreyer, et al., appear in the literature, including those listed in the bibliographies to these two papers.

The aforementioned King U.S. Pat. Nos. 4,630,611 and 4,754,753 describe X, Y and Z orthogonally displaced electrodes on the body of the endocardial pacing lead and circuitry for developing a composite EGM vector signal in order to detect changes in the vector over time and discriminate normal sinus rhythm from tachyarrhythmias.

Finally, U.S. patent application Ser. No. 611,901 entitled "Multi-Vector Pacing Artifact Detector," filed Nov. 9, 1990, and assigned to the assignee of the present application, sets forth a system for detecting the artificial pacing artifact in patients having artificially paced myocardial contractions in an external monitor employing three standard EKG leads with chest or limb electrodes.

SUMMARY OF THE INVENTION

There are a number of tasks that are normally performed either prior to or during a pacemaker follow-up session. For example, the patient's chart must be pulled and made available for reference by the clinician or physician prior to seeing the patient. Then the patient must be prepped for collecting ECG tracings. Generally, such preparation requires disrobing from the waist up and attaching ECG electrodes at the required point on the chest and other points on the body. This is followed by placing the programming head over the site of the implanted pacemaker, collecting the ECG tracings, interrogating the pacemaker, printing the report, examining all the printouts, and then determining if the pacemaker's operation is optimal. If not, then programming change(s) are usually required. Another interrogation will be made and a final printed report (which may include new ECG tracings) is captured for inclusion in the patient's records. Other tasks may also be required and performed depending on the protocol to be followed by the institution or clinic to which the patient is assigned.

One might question why all these tasks must be performed. An examination of why ECG tracings are demanded will prove instructive. Magnet and non-magnet ECG tracings are normally required for clinic use and absolutely required for remote pacemaker follow-up. In fact, an institution may not be reimbursed for follow-up services unless such ECG tracings are obtained, as occurs in the U.S. The matter of reimbursement varies from country to country; but most institutions and clinics require such tracings for their records as a matter of medical completeness, if for no other reason. Thus, such ECG tracings have become a critical component of the pacemaker followup.

As mentioned, the collection of ECG tracings require the attachment of electrodes, such as chest electrodes for in-clinic follow-ups and wrist or fingertip electrodes for a remote, transtelephonic followup. The elderly patient at home often has difficulty attaching his or her wrist or fingertip electrode so that a suitable ECG tracing is recorded and transmitted. If the difficulty persists, the patient may then be asked to come into the clinic for his/her pacer check, a far more costly visit. The in-clinic collection of ECG tracings, while it does involve a trained technician, still requires a good deal of time for attaching the ECG electrodes, ensuring they are connected appropriately to the programmer, recording the ECG tracings, removal of the ECG electrodes and, finally, storing them and/or getting them out of the way so the remainder of the follow-up session may proceed.

Unfortunately, the methods just described for collecting such ECG tracings within a clinic setting or during a remote followup have several issues. First, clinics are very sensitive to the duration of an in-clinic or remote follow-up session. The most time-consuming parts to the in-clinic procedure just described are the attachments and placement of the ECG electrodes and verification that the positioning of the electrodes results in satisfactory ECG tracings. By far, the most common issue with a remote follow-up session is the acquisition of a quality ECG tracing. It often requires several attempts by the patient to correctly position the ECG electrodes.

Secondly, the quality of the ECG is highly dependent on a number of factors independent of electrode placement such as patient movement. While the potential for patient movement is greater during and remote follow-up session than during the in-clinic session, it does occur there as well.

Thirdly, it is often difficult to determine atrial activity on ECG tracings. This is particularly true of a remote follow-up. During an in-clinic session, however, if a digital ECG recorder is being used rather than the programmer's ECG capability, the clinician may be unable to determine whether the atria are being paced due to the pacing pulse being lost between digital processing times.

Fourthly, a trained technician, clinician, or physician must validate the quality of the ECG tracings during an in-clinic or remote follow-up session. Thus, medical personnel who are untrained in ECG interpretation cannot currently be involved in either an in-clinic or remote pacemaker follow-up session.

Finally, current technology requires the use of a programmer to download all other data stored in the pacemaker's memory. It is currently impossible to download important and critical pacing data during a remote follow-up session. Similarly, an in-clinic follow-up session is needlessly prolonged by the current inability of implanted devices to telemeter data to a programmer or other devices that can receive transmitted pacemaker data and print it for study by the technician, clinician, or physician prior to actually seeing the patient.

These issues may be resolved by the use of telemetry of data to and from the implanted device. The FCC has adopted the following definition for describing wireless medical telemetry: "the measurement and recording of physiological parameters and other patient-related information via radiated bi- or unidirectional electromagnetic signals." Thus, in its broadest sense, telemetry can be defined as the art and science of conveying information from one location to another. With radio telemetry, radio signals are utilized to convey that information.

Two terms have been used to describe the type of data transmission envisaged by the current invention, Telehome and Telemedicine. Telehome care can be defined as providing monitoring (telemetry) and home health care services at a distance, using advanced telecommunications and information technology. Telemedicine is the use of telecommunications and information technology to provide clinical care at a distance. The definition of "distance" may range from several yards, such as might occur within a clinic environment or hundreds of miles as occurs in rural areas. The availability of telemedicine services in far-flung rural areas can sometimes mean the difference between life and death for patients who must travel hundreds of miles to see a nurse or doctor. Wireless technologies can be particularly beneficial in these areas because developing wireless networks may be faster and cheaper than building a wire line infrastructure.

Some emergency medical transport companies have already begun to outfit their ambulances with wireless telemedicine equipment. This equipment enables a paramedic to communicate with the emergency physician for an early assessment, well before the patient's arrival at the hospital. The telemedicine equipment can be as simple as a laptop computer with desktop videoconferencing capabilities that provide simultaneous two-way video, two-way voice, vital signs, cardiac and other data to a trauma center. This latter type of equipment is envisaged as a first step toward implementing the current invention, since wireless products such as handheld computers with Internet capabilities are becoming commonplace.

Further, medical telemetry equipment is used in hospitals and health care facilities to transmit patient measurement data to a nearby receiver, permitting greater patient mobility and increased comfort. Examples of medical telemetry equipment include heart, blood pressure and respiration monitors. The use of these devices allows patients to move around early in their recovery while still being monitored for adverse symptoms. With such devices, one health care worker can monitor several patients remotely, thus decreasing health care costs. In a similar manner, ECG and other data from an implanted device may be telemetered both intra- and extra-corporeally.

Medical telemetry equipment is increasingly relied upon in hospitals to improve health care and reduce costs. Pacing patients who formerly required the monitoring and treatment capabilities that are available only in pacemaker clinics can be monitored and treated remotely in their homes. The number of pacemaker patients with chronic medical conditions is rising due to the growth in the elderly population. For these reasons, the need for monitoring these patients outside of the clinic setting is rapidly increasing, and this need can be fulfilled with medical telemetry equipment.

The Leadless Fully Automatic Pacemaker Followup (LFAPF) system of the present invention addresses all the issues described above and makes use of the type of telemetry described above. Briefly, this novel process involves the transmission of a signal to the pacemaker that may trigger one or any number of transmissions. ECG tracings can be transmitted for processing and printing, as well as the contents of the pacemaker's memory including pacemaker diagnostics such as the number and duration of mode switches. Such triggering would also include activation of a number of diagnostic operations, such as the measurement of the stimulation threshold and/or Capture Management.

DETAILED DESCRIPTION OF THE DRAWINGS

Figure 1:
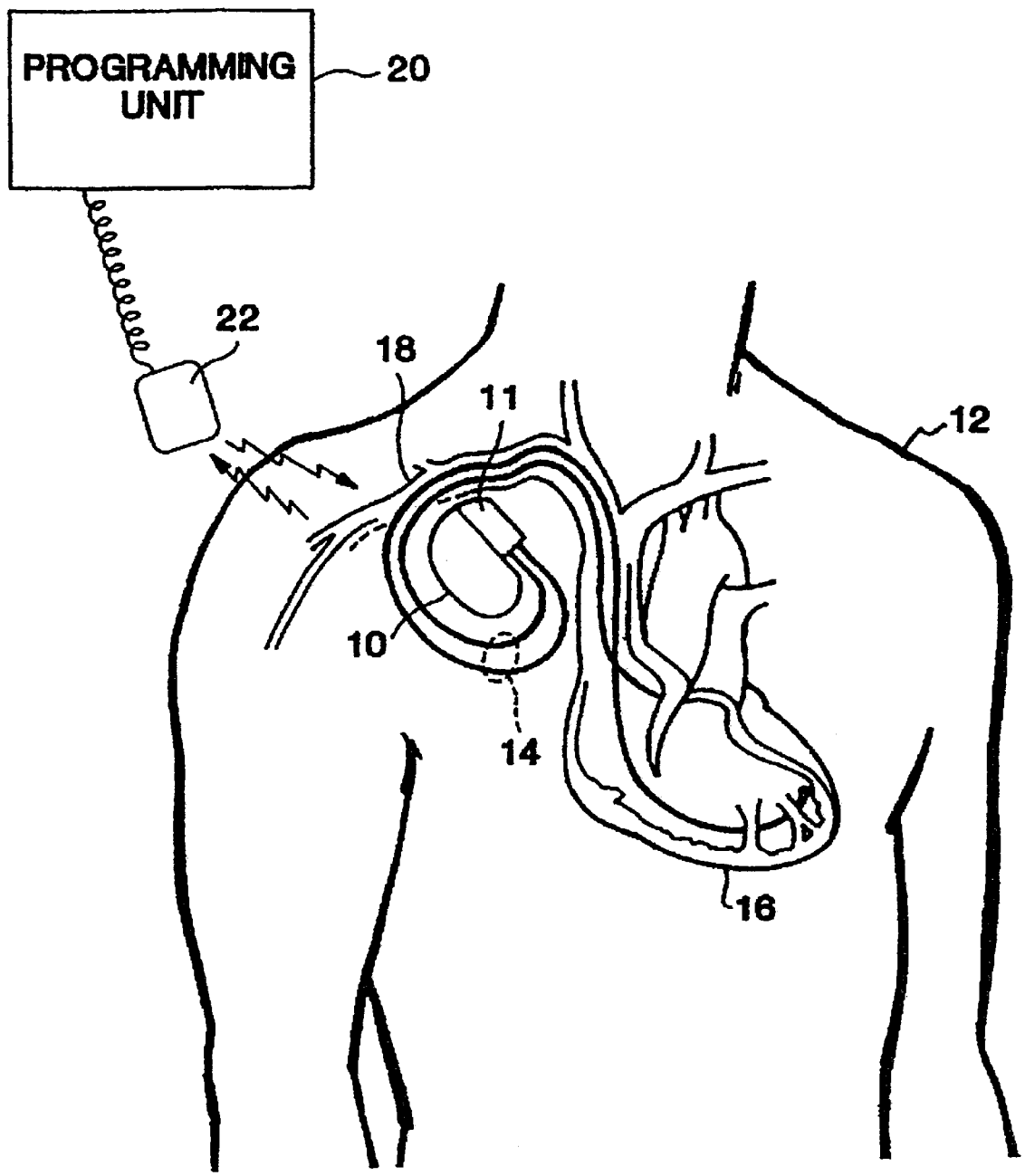
FIG. 1 is an illustration of a body-implantable device system in accordance with the present invention, including a hermetically sealed device implanted in a patient and an external remote programming/receiver unit.

FIG. 1 is an illustration of an implantable medical device system adapted for use in accordance with the present invention. The medical device system shown in FIG. 1 includes an implantable device 10—a pacemaker in this embodiment-that has been implanted in a patient 12. In accordance with conventional practice in the art, pacemaker 10 is housed within a hermetically sealed, biologically inert outer casing, which may itself be conductive so as to serve as an indifferent electrode in the pacemaker's pacing/sensing circuit. One or more pacemaker leads, collectively identified with reference numeral 14 in FIG. 1 are electrically coupled to pacemaker 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to heart 16. As will be appreciated by those of ordinary skill in the art, leads 14 may be implanted with its distal end situated in the atrium and/or ventricle of heart 16.

Although the present invention will be described herein in one embodiment that includes a pacemaker, those of ordinary skill in the art having the benefit of the present disclosure will appreciate that the present invention may be advantageously practiced in connection with numerous other types of implantable medical device systems.

Also depicted in FIG. 1 is an external programming unit 20 for non-invasive communication with implanted device 10 via uplink and downlink communication channels, to be hereinafter described in further detail. Associated with programming unit is a transmitter/receiver telemetry circuit for facilitating two-way communication between implanted device 10 and programmer 20.

Figure 2:
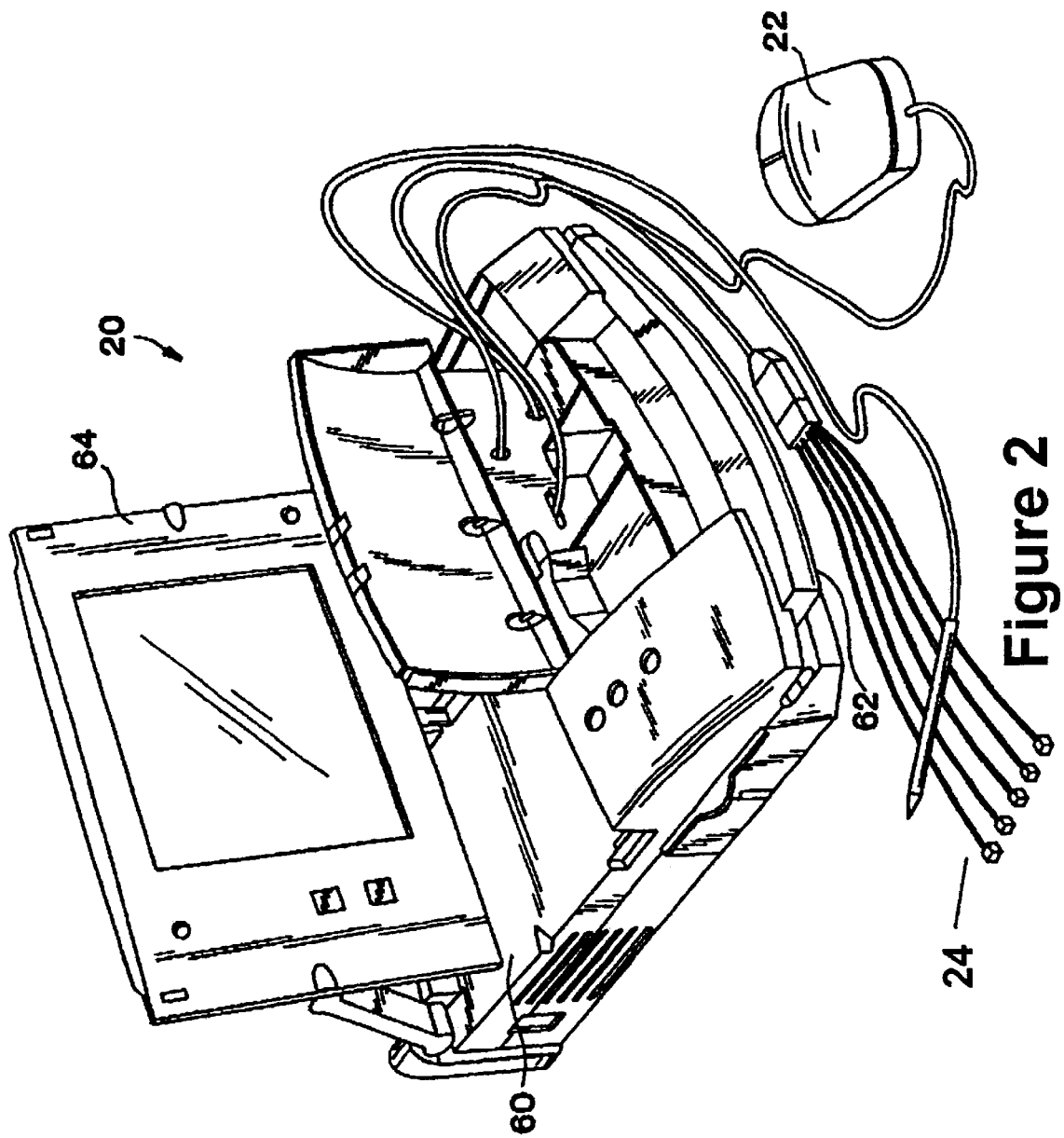
FIG. 2 is a perspective view of the remote programming unit of FIG. 1.

FIG. 2 is a perspective view of a remote programming unit 20 in accordance with the presently disclosed invention. Internally, programmer 20 includes a processing unit (not shown in the Figure) that in accordance with the presently disclosed invention is a personal computer type motherboard, e.g., a computer motherboard including an Intel Pentium 3 microprocessor and related circuitry such as digital memory. Additionally, programmer 20 also includes a telemetry unit (not shown in this Figure) that in accordance with the presently disclosed invention functions as the transmitter/receiver for sending triggering commands to the implanted device shown in FIG. 1 as well as receiving transmissions from implanted device. The details of design and operation of the programmer's computer system will not be set forth in detail in the present disclosure, as it is believed that such details are well-known to those of ordinary skill in the art. Referring to FIG. 2, programmer 20 comprises an outer housing 60, which is preferably made of thermal plastic or another suitably rugged yet relatively lightweight material. A carrying handle, designated generally as 62 in FIG. 2, is integrally formed into the front of housing 60. With handle 62, programmer 20 can be carried like a briefcase.

An articulating display screen 64 is disposed on the upper surface of housing 60. Display screen 64 folds down into a closed position (not shown) when programmer 20 is not in use, thereby reducing the size of programmer 20 and protecting the display surface of display 64 during transportation and storage thereof.

A floppy disk drive is disposed within housing 60 and is accessible via a disk insertion slot (not shown). A hard disk drive is also disposed within housing 60, and it is contemplated that a hard disk drive activity indicator, (e.g., an LED, not shown) could be provided to give a visible indication of hard disk activation.

As would be appreciated by those of ordinary skill in the art, it is necessary to make programming changes to the implanted device to optimize pacing therapy. To accomplish this task and provide ease of programming, programmer 20 is equipped with touch pen 24, which may be used to touch display screen 64 to change parameters and access transmitted data.

In accordance with the present invention, programmer 20 is equipped with an internal printer (not shown) so that a hard copy of a patient's transmitted ECG or data displayed on the programmer's display screen 64 can be generated. Several types of printers, such as the AR-100 printer available from General Scanning Co., are known and commercially available.

As would be appreciated by those of ordinary skill in the art, display screen 64 is operatively coupled to the computer circuitry disposed within housing 60 and is adapted to provide a visual display of graphics and/or data under control of the internal computer.

The programmer may be equipped with a telemetry unit (not shown) to send and receive signals that trigger the transfer of data from the implanted device to the programmer. In the system envisaged, a pacemaker technician would program the command to uplink data such as the ECG and/or test and diagnostic data as the patient sits in the waiting room. These data would appear on display screen 64 for analysis by the technician, clinician, or physician.

Figure 3:
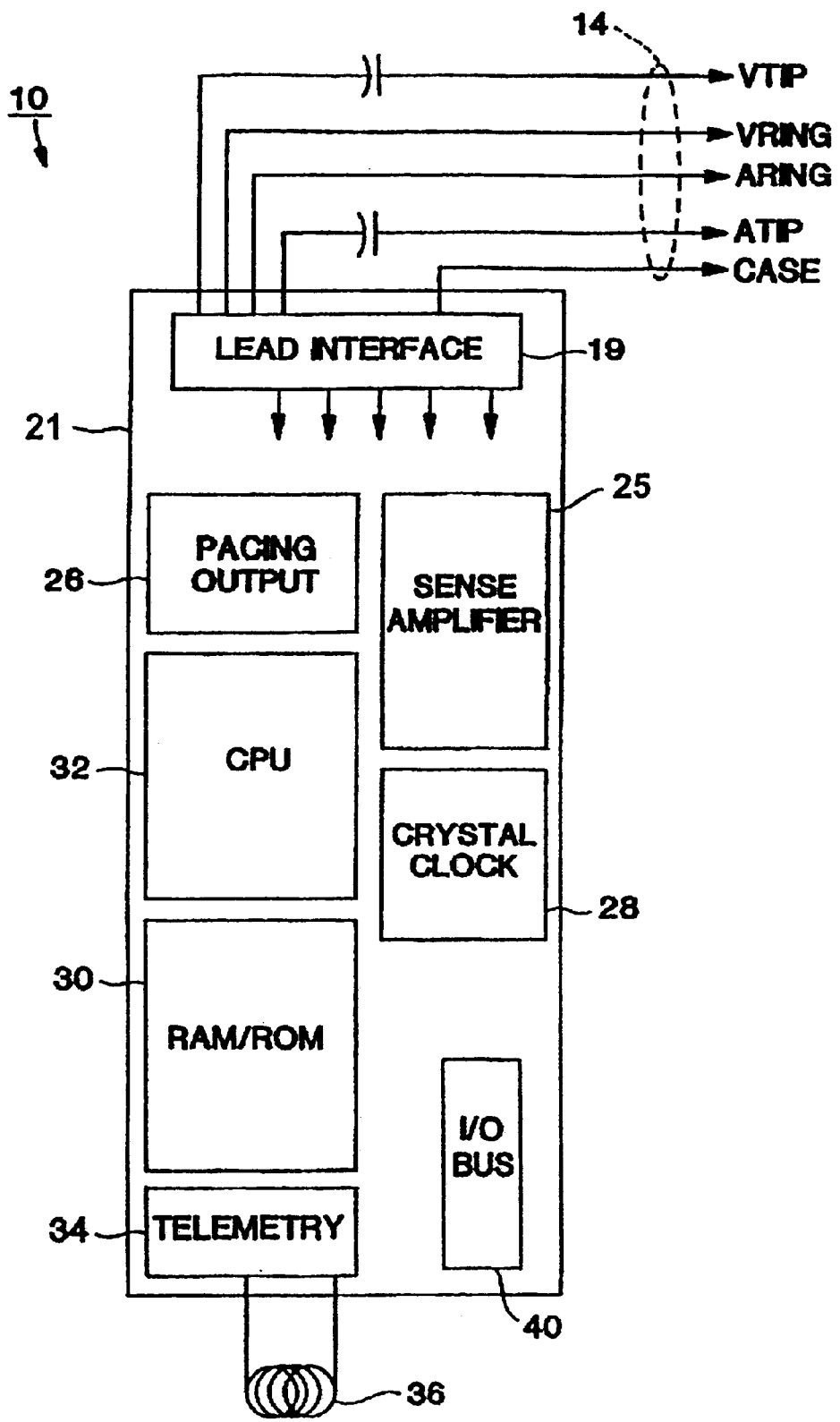
FIG. 3 is a block diagram of the implanted device from FIG. 1.

FIG. 3 is a block diagram of the electronic circuitry that makes up pulse generator 10 in accordance with the presently disclosed invention. As can be seen from FIG. 3, pacemaker 10 comprises a primary stimulation control circuit 20 for controlling the device's pacing and sensing functions. The circuitry associated with stimulation control circuit 20 may be of conventional design, in accordance, for example, with what is disclosed U.S. Pat. No. 5,052,388 issued to Sivula et al., "Method and apparatus for implementing activity sensing in a pulse generator." To the extent that certain components of pulse generator 10 are conventional in their design and operation, such components will not be described herein in detail, as it is believed that design and implementation of such components would be a matter of routine to those of ordinary skill in the art. For example, stimulation control circuit 20 in FIG. 3 includes sense amplifier circuitry 24, stimulating pulse output circuitry 26, a crystal clock 28, a random-access memory and read-only memory (RAM/ROM) unit 30, and a central processing unit (CPU) 32, all of which are well-known in the art. Pacemaker 10 also includes internal telemetry transmission and receiver circuitry 34 and 36 for uplink and downlink communication with external telemetry unit such as programmer/control unit 20, as described in FIG. 2 in greater detail. Such transmissions, however, are not limited to the programmer. The receiver could be a hand-held device such as a Palm Pilot® which receives the telemetered data and then uploads such data to the Internet directly or through a laptop or desktop computer. Additionally, ECG data may be transmitted to another co-implanted device for its use in deciding whether to apply or withhold its therapy.

With continued reference to FIG. 3, pulse generator 10 is coupled to one or more leads 14 which, when implanted, extend transvenously between the implant site of pulse generator 10 and the patient's heart 16, as previously noted with reference to FIG. 1. Physically, the connections between leads 14 and the various internal components of pulse generator 10 are facilitated by means of a conventional connector block assembly 11, shown in FIG. 1. Electrically, the coupling of the conductors of leads and internal electrical components of pulse generator 10 may be facilitated by means of a lead interface circuit 19 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of pulse generator 10, as would be familiar to those of ordinary skill in the art. For the sake of clarity, the specific connections between leads 14 and the various components of pulse generator 10 are not shown in FIG. 3, although it will be clear to those of ordinary skill in the art that, for example, leads 14 will necessarily be coupled, either directly or indirectly, to sense amplifier circuitry 24 and stimulating pulse output circuit 26, in accordance with common practice, such that cardiac electrical signals may be conveyed to sensing circuitry 24, and such that stimulating pulses may be delivered to cardiac tissue, via leads 14. Also not shown in FIG. 3 is the protection circuitry commonly included in implanted devices to protect, for example, the sensing circuitry of the device from high voltage stimulating pulses.

As previously noted, stimulation control circuit 20 includes central processing unit 32 which may be an off-the-shelf programmable microprocessor or micro controller, but in the present invention is a custom integrated circuit. Although specific connections between CPU 32 and other components of stimulation control circuit 20 are not shown in FIG. 3, it will be apparent to those of ordinary skill in the art that CPU 32 functions to control the timed operation of stimulating pulse output circuit 26 and sense amplifier circuit 24 under control of programming stored in RAM/ROM unit 30. It is believed that those of ordinary skill in the art will be familiar with such an operative arrangement.

With continued reference to FIG. 3, crystal oscillator circuit 28, in the presently preferred embodiment a 32,768-Hz crystal controlled oscillator provides main timing clock signals to stimulation control circuit 20. Again, the lines over which such clocking signals are provided to the various timed components of pulse generator 10 (e.g., microprocessor 32) are omitted from FIG. 3 for the sake of clarity.

It is to be understood that the various components of pulse generator 10 depicted in FIG. 3 are powered by means of a battery (not shown) that is contained within the hermetic enclosure of pacemaker 10, in accordance with common practice in the art. For the sake of clarity in the Figures, the battery and the connections between it and the other components of pulse generator 10 are not shown.

Stimulating pulse output circuit 26, which functions to generate cardiac stimuli under control of signals issued by CPU 32, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits that would be suitable for the purposes of practicing the present invention.

Sense amplifier circuit 24, which is of conventional design, functions to receive electrical cardiac signals from leads 14 and to process such signals to derive event signals reflecting the occurrence of specific cardiac electrical events, including atrial contractions (P-waves) and ventricular contractions (R-waves). CPU provides these event-indicating signals to CPU 32 for use in controlling the synchronous stimulating operations of pulse generator 10 in accordance with common practice in the art. In addition, these event-indicating signals may be communicated, via uplink transmission, to external programming unit 20 for visual display to a physician or clinician.

Those of ordinary skill in the art will appreciate that pacemaker 10 may include numerous other components and subsystems, for example, activity sensors and associated circuitry. The presence or absence of such additional components in pacemaker 10, however, is not believed to be pertinent to the present invention, which relates primarily to the implementation and operation of communication subsystem 34 in pacemaker 10, and an associated communication subsystem in external unit 20.

Figure 4:
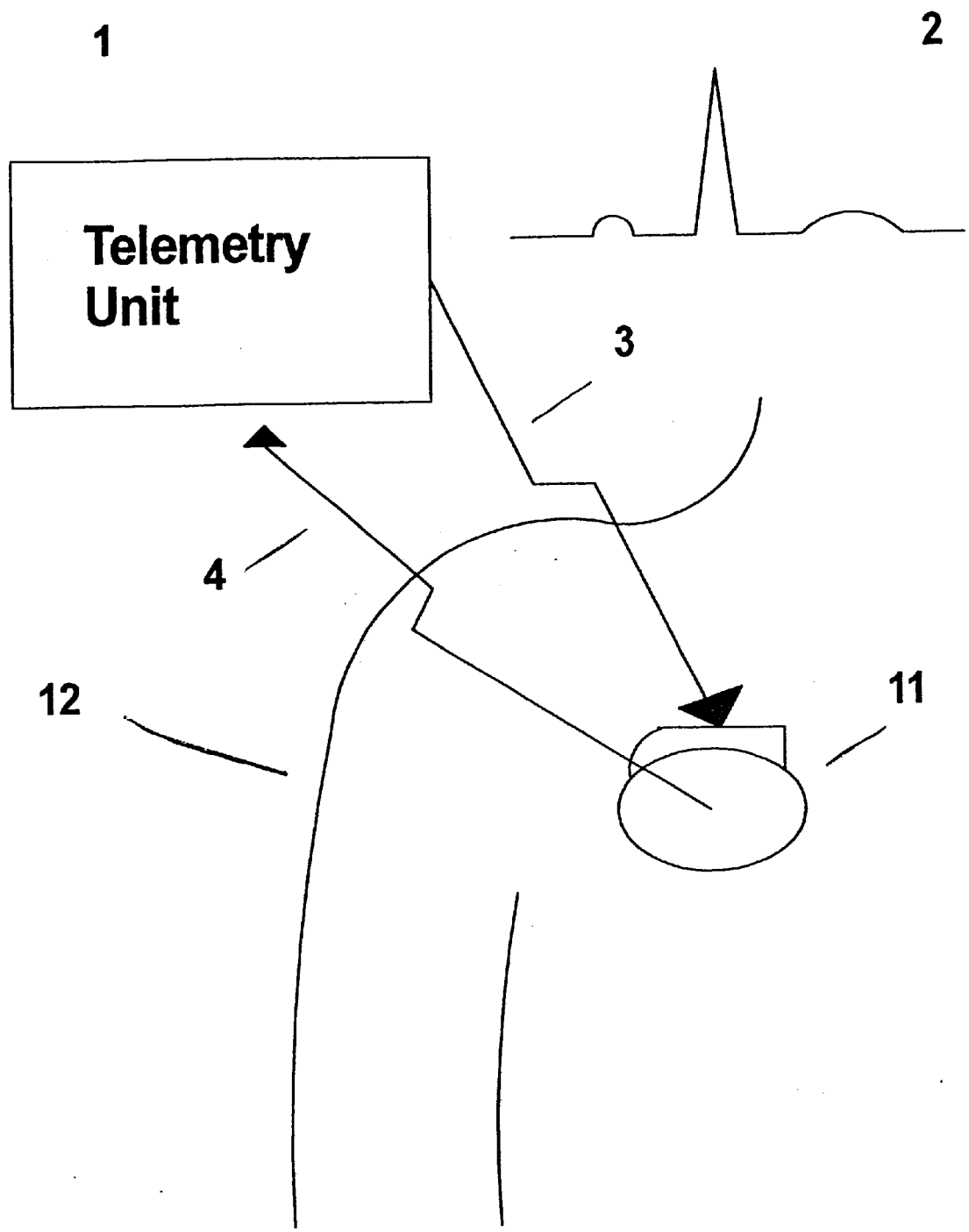
FIG. 4 is an illustration of a body-implantable device and associated telemetry unit for the purpose of transmitting an ECG tracing extra-corporeally.

FIG. 4 is an illustration of a body-implantable device and associated telemetry unit for the purpose of transmitting an ECG tracing extra-corporeally. Implanted device 11, which may be an implanted pacemaker, PCD, or other such device, is implanted in patient 12. A leadless fully automatic pacemaker follow-up (LFAPF) may begin with or be limited to a simple transmission of ECG tracing 2. To access ECG tracing 2, Telemetry unit 1 transmits signal 3 to implanted device 11 to uplink and transmit digitally encoded ECG data 4 for decoding and display as tracing. The LFAPF can be triggered either locally or remotely, that is, within the confines of a waiting room as the patient is seated prior to being escorted to an examining room or pacemaker follow-up center. A remote transmission could occur over the Internet or phone with the patient being seated near an uplink device (not shown), such as a telephone transmission unit, Palm Pilot, laptop, desktop, etc. The transmission of the ECG data may be to a central database located within a clinic for printing or examination on a computer screen or to a programmer equipped to receive these types of data and then print them out.

Figure 5:
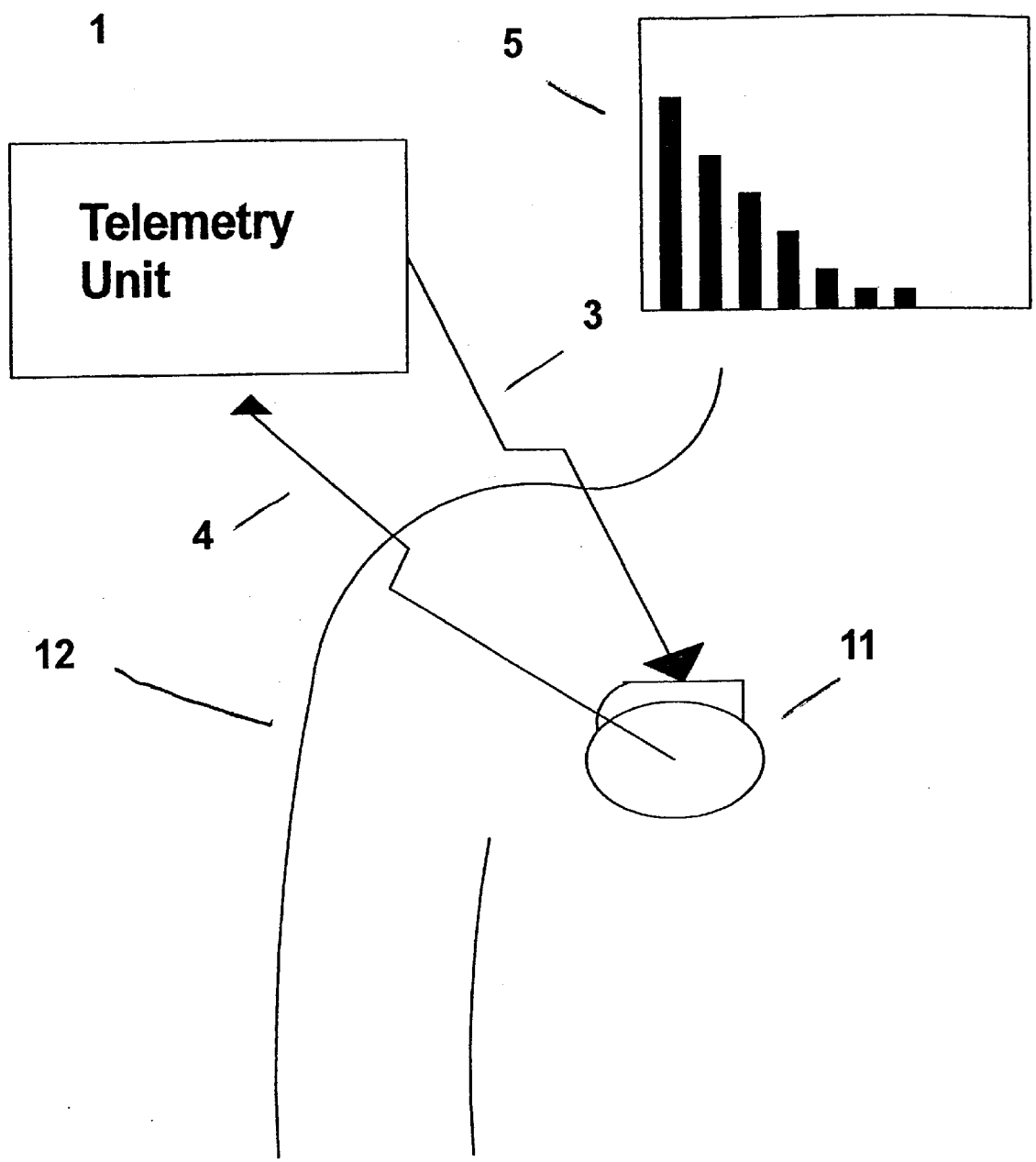
FIG. 5 is an illustration of a body-implantable device and associated telemetry unit for the purpose of transmitting stored and testing data extra-corporeally.

FIG. 5 is an illustration of a body-implantable device and associated telemetry unit for the purpose of transmitting stored and testing data extra-corporeally. In this embodiment, the LFAPF would provide a much fuller array of data. Implanted device 11, which may be an implanted pacemaker, PCD, or other such device, is implanted in patient 12. A more complete leadless fully automatic pacemaker follow-up (LFAPF) initiated by telemetry unit 1 consists of a series of commands, collectively identified as 3.

First, a full interrogation of the pacemaker's memory takes place with the results transmitted and stored in a patient session file. One of the pieces of data would consist of histograms such as displayed in 5. The remaining operations are not shown since those familiar with the state of the art will be able to visualize the type of data that would be displayed as well as the type of tests that are being described.

Second, upon completion of the interrogation, the magnet mode is invoked and the Subcutaneous Electrode Array (SEA) collects an ECG tracing for a specified number of seconds. The strip is simultaneously transmitted to the patient's file and annotated with markers to show pacing, sensing, etc. This strip then becomes available for display and printing.

Thirdly, the magnet mode is suspended and the SEA collects a non-magnet ECG tracing that is processed in the same manner as the magnet strip.

Fourthly, a ventricular capture auto-threshold search is triggered. This search is documented by an SEA ECG tracing that is marked and annotated for display and/or printing and then saved in the patient's file.

Fifthly, the atrial capture auto-threshold search is then invoked. This search is documented by an SEA ECG tracing that is marked and annotated for display and/or printing and then saved in the patient's file.

Sixthly, the ventricular sensing threshold is automatically determined. The results are documented by an SEA ECG tracing that is annotated with the sensing threshold data.

Next, an atrial sensing threshold is determined and documented.

Finally, a printed report is generated, one that includes all of the data that had been sent to the patient session file. The technician, clinician, or physician may use this report to prepare for the meeting with the pacemaker patient. The time saved will be used advantageously to discuss the patient's concerns about the pacing therapy and to quickly make any changes to the pacemaker's pacing parameters, thereby optimizing the pacing operation to match the patient's needs.

Figure 6:
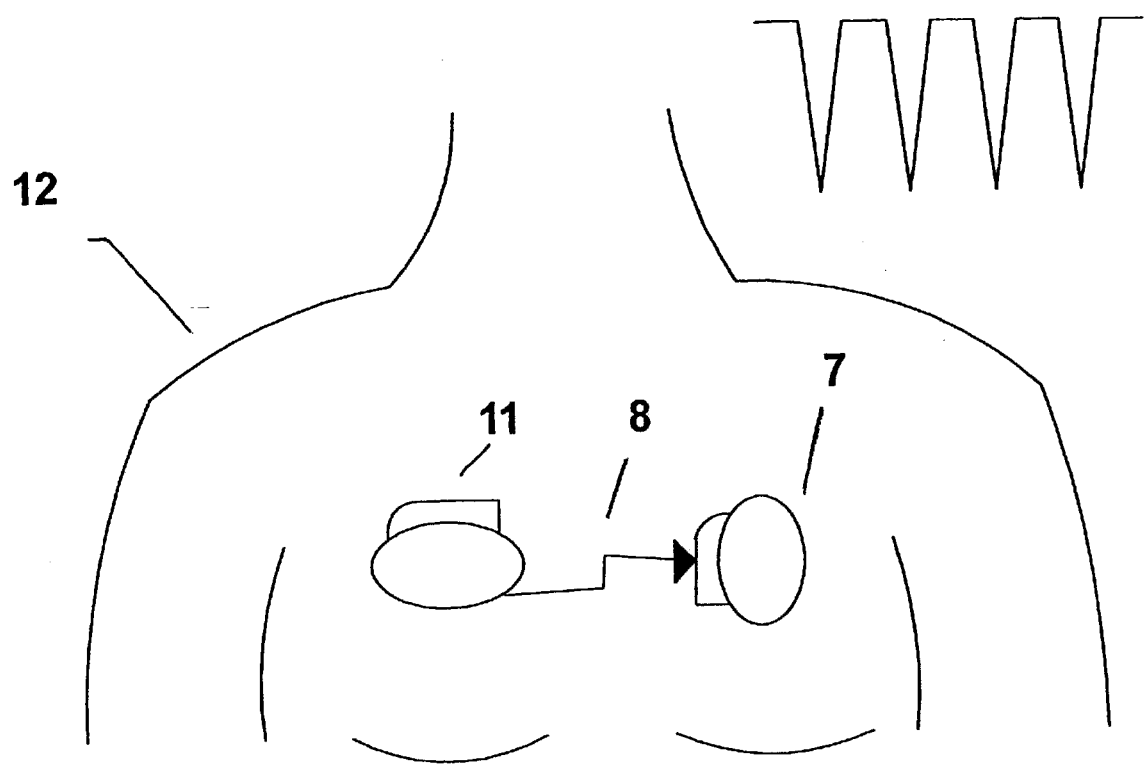
FIG. 6 is an illustration of a body-implantable device and a co-implanted device for the purpose of transmitting an ECG tracing intra-corporeally.

FIG. 6 is an illustration of a body-implantable device and a co-implanted device for the purpose of transmitting an ECG tracing intra-corporeally. In addition to extra-corporeal transmission of ECG data, it is also possible to telemeter such data 8 from implanted device 11 equipped with a subcutaneous electrode array to another co-implanted device 7 that may advantageously use these data.

An example of such use might consist of a very basic implanted cardioverter-defibrillator as co-implanted device 7 that has been implanted to treat and/or shock the heart to break a recently diagnosed ventricular arrhythmia. An SEA-equipped bradycardia pacemaker 11 had been previously implanted to treat a commonly indicated condition such as third degree block. In addition to providing pacing support, pacemaker 11 also has the capability of transmitting ECG tracings to co-implanted PCD 7. Assume, for example, pacemaker 11 detects ventricular arrhythmia 6. This ECG tracing is transmitted to co-implanted PCT 7 to provide PCD 7 with data to take action such as a response by supplying a cardioversion pulse synchronized to one of the ventricular tachycardia events so as to restore the patient's heart to a normal rhythm and rate.

Thus, while LFAPF may be used in extra-corporeal fashion as its primary embodiment, the very same technology may also be used intra-corporeally to the advantage of the patient and the medical community. The medical benefits and cost savings that would accrue to the health insurance underwriters would be substantial whether the embodiment be intra- or extra-corporeal.

Various modifications, equivalent processes, as well as numerous structures to which the present invention may be applicable will be readily apparent to those of skill in the art to which the present invention is directed upon review of the present specification. The claims are intended to cover such modifications and devices.

What is claimed is:

1. A leadless fully automatic pacemaker follow-up (LFAPF) system including a plurality of implantable medical devices with adjustable transmission for cardiac data, the system comprising:

a wireless transmission unit extra-corporeally dispensed having a data communications link with at least one of said plurality of implantable medical devices;

means for transmitting a signal to said at least one of said plurality of implantable medical devices to uplink and transmit the cardiac data;

means for initiating said wireless transmission unit to send said signal to said at least one of said plurality of implantable medical devices via said data communications link; and means for transmitting cardiac data from one of said plurality of implantable medical devices to another one of said plurality of implantable medical devices.

2. The system of claim 1 wherein said wireless transmission unit includes a telemetry unit to transmit said signal to said at least one of said plurality of implantable medical devices to uplink and transmit the cardiac data.

3. The system of claim 1 wherein said adjustable transmission includes one of a full interrogation and a partial interrogation regimen.

4. The system of claim 1 wherein the cardiac data includes digitally encoded ECG data.

5. The system of claim 4 wherein said ECG data is decoded and displayed as tracing by the LFAPF device.

6. A LFAPF device including a plurality of implanted medical devices forming an arrangement for transmitting cardiac data intra-corporeally, the arrangement comprising:

a first implanted device;

a second implanted device; and means for transmitting cardiac data from said first implanted device to said second implanted device.

7. The arrangement of claim 6 wherein said first implanted device is a cardiac pacemaker.

8. The arrangement of claim 6 wherein said second implanted device is a cardioverter-defibrillator.

9. The arrangement of claim 6 wherein said cardiac data includes ECG tracings.

10. The arrangement of claim 6 wherein said means for transmitting includes subcutaneous electrode arrays.

11. A method for collecting and transmitting a plurality of physiological data from a memory bank of an implanted medical device (IMD) in cooperation with a leadless fully automatic pacemaker follow-up (LFAPF) unit, the method comprising:

initiating at least one command to start the collecting method;

interrogating the memory bank of the IMD;

collecting said plurality of physiological data; and transmitting the data to a patient's file.

12. The method of claim 11 wherein a telemetry unit is implemented to initiate the at least one command.

13. The method of claim 11 wherein the memory bank interrogation involves substantially full interrogation of the IMD memory bank including transmission of results in a patient session file.

14. The method of claim 11 wherein a printed report is generated including all the data transmitted to the patient's file.

15. The method of claim 11 wherein a non-magnet mode is invoked by suspending a magnet mode to collect another one of said plurality of physiological data.

16. The method of claim 15 wherein said another one of such data includes a non-magnet ECG tracing.

17. The method of claim 11 wherein a magnet mode is invoked and SEA (subcutaneous electrode array) is implemented to collect at least one of said plurality of physiological data for a set of time intervals.

18. The method of claim 17 wherein said at least one of said plurality of physiological data includes an ECG tracing.

19. The method of claim 17 wherein said set of time intervals includes a number of seconds.

20. The method of claim 11 wherein specific types of said plurality of physiological data are collected after triggering a search in the memory bank.

21. The method of claim 20 wherein said specific types of data include at least one of a ventricular capture auto-threshold, atrial capture auto-threshold, a ventricular sensing threshold, and an atrial sensing threshold.

22. The method of claim 21 wherein said ventricular sensing threshold is automatically determined.

* * * * *